(12) United States Patent
Shankar et al.

(10) Patent No.: US 12,213,868 B1
(45) Date of Patent: Feb. 4, 2025

(54) APPARATUS AND METHOD FOR FILAMENT WINDING OF BIOCOMPATIBLE THREADS AND MANUFACTURED FABRIC PRODUCT

(71) Applicant: CollaMedix Inc., Cleveland, OH (US)

(72) Inventors: Subba Shankar, Shaker Heights, OH (US); Michael A. Mastran, Tallmadge, OH (US); Ozan Akkus, Shaker Heights, OH (US)

(73) Assignee: CollaMedix Inc., Cleveland, OH (US)

( * ) Notice: Subject to any disclaimer, the term of this patent is extended or adjusted under 35 U.S.C. 154(b) by 562 days.

(21) Appl. No.: 17/586,532

(22) Filed: Jan. 27, 2022

Related U.S. Application Data

(60) Provisional application No. 63/147,830, filed on Feb. 10, 2021.

(51) Int. Cl.
*A61F 2/00* (2006.01)
*A61L 27/24* (2006.01)
*A61L 27/58* (2006.01)
*D04B 21/12* (2006.01)

(52) U.S. Cl.
CPC ............ *A61F 2/0063* (2013.01); *A61L 27/24* (2013.01); *A61L 27/58* (2013.01); *D04B 21/12* (2013.01); *A61F 2002/0068* (2013.01); *D10B 2211/06* (2013.01); *D10B 2401/12* (2013.01); *D10B 2509/08* (2013.01)

(58) Field of Classification Search
CPC .......... A61F 2/0063; A61F 2002/0068; A61L 27/24; A61L 27/58; D04B 21/12; D10B 2211/06; D10B 2401/12; D10B 2509/08
See application file for complete search history.

(56) References Cited

U.S. PATENT DOCUMENTS

| | | | |
|---|---|---|---|
| 5,660,348 | A | 8/1997 | Sansone |
| 7,083,644 | B1 | 8/2006 | Moroni |
| 10,017,868 | B2 * | 7/2018 | Akkus ................ A61L 27/26 |
| 2010/0311949 | A1 | 12/2010 | Akkus |
| 2013/0225669 | A1 | 8/2013 | Michael |
| 2018/0133950 | A1 | 5/2018 | Erol |
| 2018/0312988 | A1 | 11/2018 | Akkus |
| 2019/0262496 | A1 | 8/2019 | Zender |
| 2021/0108321 | A1 | 4/2021 | Akkus |
| 2021/0228771 | A1 | 7/2021 | Akkus |

FOREIGN PATENT DOCUMENTS

| | | | | |
|---|---|---|---|---|
| WO | WO-2005030137 A2 * | 4/2005 | .......... | A61K 31/555 |
| WO | WO-2005115272 A2 * | 12/2005 | ............... | A61F 2/06 |
| WO | WO-2010048281 A1 * | 4/2010 | ............. | A61L 27/48 |

* cited by examiner

Primary Examiner — Daniel H Lee
(74) Attorney, Agent, or Firm — Keusey & Associates, P.C.

(57) ABSTRACT

A system and method for determining a mesh layout and manufacturing an implantable mesh. A support surface with pins is provided in a configuration that corresponds to the mesh layout. A biocompatible filament is wound around the pins to provide a macroporous mesh. The completed weave is treated with a solution to bond intersection points of filament, then sterilized and packaged to provide an implantable mesh.

17 Claims, 7 Drawing Sheets

APPARATUS AND METHOD FOR FILAMENT WINDING OF BIOCOMPATIBLE THREADS AND MANUFACTURED FABRIC PRODUCT

CROSS REFERENCE TO RELATED APPLICATIONS

This application claims the benefit under 35 U.S.C. § 119 (e) from U.S. Provisional Patent Application No. 63/147,830 entitled Apparatus and Method for Filament Winding of Biocompatible Threads and Manufactured Fabric Product filed on Feb. 10, 2021.

BACKGROUND OF THE INVENTION

1. Field of the Invention

The invention relates to an apparatus and method for filament winding of biocompatible threads and manufactured fabric product

2. The Prior Art

To create implantable slings for female stress urinary incontinence treatment or other devices for soft tissue repair and support a strong, macroporous fabric made from biocompatible threads must be provided.

U.S. Pat. No. 7,083,644 entitled Implantable Prostheses with Improved Mechanical and Chemical Properties provides implantable textile prostheses with chemical and mechanical properties that are superior to previous polyethylene terephthalate (PET) materials. The proposed naphthalene dicarboxylate (NDC) derivative can be treated with more powerful sterilization methods and may be coated with a bio-absorbable coating such as collagen albumin, elastin and the like. The NDC yarns undergo traditional weaving, braiding, knitting and winding processes. The filament winding construction is followed by treatment with solvated polyurethane elastomer to glue the yarns together. The Patent does not mention pores or the need to control pore size.

The WIPO Publication WO2005/1152 entitled Composite Medical Textile Material and Implantable Devices Made Therefrom discloses polytetrafluoroethylene (PTFE) or expanded polytetraflouroethylene (ePTFE) yarns. The yarns are fashioned into a woven textile portion and a knitted textile portion which are then layered together to provide improved mechanical properties which resists dilation. The resulting composite textile material may be coated with bio-absorbable collagen, albumin, elastin. The coatings may be treated with a bioactive agent or a sealant that cross-links the bio-coating to the composite textile surface.

The WIPO Publication WO2010/048281 entitled Composite Biomimetic Materials discloses wet spinning collagen fibers which are extruded and wound on a PVC pipe that rotates and translates automatically. Winding onto rectangular frames is proposed with computer control of spacing, angle, frame translation speed, translation distance and rotation speed. Collagen may be blended with polymers or biopolymers and electrospun. Collagen may be set in cylindrical forms with its voids filled with a solution of matrix material and molded to create tubular grafts. In order to increase the strength of the grafts, collagen fibers are embedded into a film formed from elastin-mimetic protein.

U.S. Pat. No. 5,660,348 entitled Computer Controlled Filament Winding System having Tensioning Device allows for filament winding on long rods by mounting the long rod to stationary supports to prevent it from sagging. The filament winding head traverses axially along the rod and rotates about the rod to wind filament with precise spacing. The system is limited to providing one pass of filament in a spiral configuration along the rod.

Accordingly, it would be desirable to overcome the limitations of the prior art and provide biocompatible mesh for a variety of soft tissue repair.

There would be considerable medical benefits if the mesh could be fashioned into macroporous fabric having controllable pore size.

It would further be desirable to create the mesh from completely bio-absorbable filament.

Another advantage would be to provide a fabric production method that minimizes the use of thread.

It would be desirable to produce such fabric with the threads aligned as closely as possible to the load axis of the tissue being repaired.

A further advantage would be to provide such mesh as implantable slings tailored for female urinary stress incontinence treatment.

SUMMARY OF THE INVENTION

To create implantable devices for soft tissue repair and support we must be able to make a strong, macroporous fabric from biocompatible threads, for example, collagen threads. Weaving or knitting of the threads is possible, but these methods consume a great deal of thread on start up. In addition, much of the thread is not oriented along the primary load axis of the material. We have previously found in animal experiments that new collagen is laid down in vivo parallel to the collagen threads of the fabric. Therefore, we have been developing a fabric production method that minimizes the use of thread while aligning most threads as closely as possible to the load axis. We have found that filament winding achieves these goals. One particularly useful application for the mesh according to the invention is the creation of implantable slings for female stress urinary incontinence treatment.

These and other objects are achieved according to one embodiment of the invention featuring a system for custom manufacturing an implantable mesh including a microprocessor, a support surface having pins, and a spool of biocompatible filament with a tensioner that feeds filament through a dispenser tip as the microprocessor translates the support surface with respect to the dispenser tip in two dimensions independent from each other to wind the filament around the pins to form an implantable macroporous mesh.

The system includes a non-transitory machine readable medium storing a set of instructions for execution by microprocessor to determine a custom mesh layout having filament retention points. The mesh layout optimizes filament usage and provides preselected pore size and a portion of filament at an angular offset with respect to an edge of the mesh layout that is adapted to align approximately to a load axis that the macroporous mesh will be subject to following implantation.

The set of instructions further converts the mesh layout to a computer aided design (CAD) module which is used for computer aided manufacturing (CAM) to machine the support surface with integrally formed pins in locations corresponding to the filament retention points of the mesh layout. The system further includes a die machined from the CAD/CAM module, wherein the die is used to mold a support surface with integrally formed pins. The system further includes a 3D printed support surface generated from the CAD/CAM module with integrally formed pins or apertures to removably insert pins In a preferred embodiment, the support surface includes a tube with pins in locations corresponding to the filament retention points of the mesh layout mounted on a mandrel having a central axis. The mandrel is coupled to a rotary drive which is mounted on a linear drive. The set of instructions rotates the mandrel clockwise and counter clockwise while linearly displacing the mandrel back and forth along the central axis. The pins may be integrally formed with the tube. Alternatively, the tube may include apertures, wherein the pins may be removably inserted into the apertures so that one tube can wind different mesh layouts.

The system further includes a supply of solution to treat the macroporous mesh to dissolve an outer surface of the filament so that intersecting filament sections bind to each other. The solution supply may be provided as a solution bath in which the tube with completed macroporous mesh is removed from the mandrel and dipped into the solution bath. The solution is an acid solution.

The tube includes right marginal pins and left marginal pins; and may include further pins located within the left and right margins. The axial distance between the left and right marginal pins defining the mesh width. The circumferential distance between pins of one side defining two parallel sides of a diamond that encloses the pores. The pins may be equally spaced from each other; the pins may be unequally spaced from each other. One group of pins may be equal spaced from one another while another group of pins may be unequal spaced from one another to provide different thread density at various locations on the mesh. The filament winds alternately around a right marginal pin then a left marginal pin. A border of filament may be provided that winds around the pins to form a perimeter around the mesh. The mandrel can accept tubes, rings or cylinders of various sizes and pin configurations that can be quickly attached or removed The macroporous mesh may be cut to remove it from the pins. Alternatively, the pins may be removed from the tube, and a macroporous sleeve slid axially off the tube. The system may include a sterilization station is provided to sterilize the removed mesh. The filament is a bioabsorbable filament, for example, made from collagen. In a preferred embodiment the filament consists of collagen, particularly electrochemically compacted collagen. The system may include a packaging station to enclose and protect the sterilized mesh.

In another aspect of the invention, there is provided a method of manufacturing an implantable mesh including determining a mesh layout having filament retention points and providing a support surface with pins in a configuration that corresponds to the filament retention points. A biocompatible filament is fed by a tensioner to a dispenser tip. The support surface is translated with respect to the dispenser tip, wherein the support surface is translated in two dimensions independent from each other to wind the biocompatible filament around the pins to form an implantable macroporous mesh having a pore size based on the determined mesh layout.

The translating step includes winding the biocompatible filament around the pins in a preselected order to arrange some portions of the filament at an angular offset with respect to an edge of the implantable mesh, wherein the angularly offset portions of the filament are adapted to align approximately to a load axis that the macroporous mesh will be subject to following implantation.

The filament comprises a bio-absorbable material, for example, the filament consists of collagen. In a preferred embodiment, the filament comprises electrochemically aligned collagen. Following said translating step the method further comprises the step of contacting the formed mesh with a biocompatible solution to dissolve the biocompatible filament so that intersecting filament sections bond to each other. The filament consists of bioabsorbable compacted aligned collagen dispensed by the tensioner to the dispenser tip at a tension within the range of 0.1 N to 1 N. After being wound, the mesh is contacted with an acidic solution having a pH in the range of 2.5 to 3.5.

The support surface is machined to provide fixed pins in the configuration, and wherein filament is would around the pins to form a perimeter for the mesh layout. The support surface comprises a cylindrical tube mounted on a mandrel having a central axis, and wherein translating the support surface comprises displacing the mandrel along the central axis and independently rotating the mandrel around the central axis. The step of providing a support surface further comprises fabricating the tube with apertures so that pins can be removably placed in various configurations.

Following the translating step the method further comprises the step of dipping the mandrel into a solution to dissolve the biocompatible filament so that intersecting filament sections bond to each other. Alternatively, following said translating step the method further comprises the step of contacting the formed mesh with a solution to dissolve the biocompatible filament so that intersecting filament sections bond to each other. Following the contacting step, the method further includes the step of removing the mesh from the mandrel as a sleeve. Following the removing step, the method further includes the step of sterilizing the mesh. Following the sterilizing step, the method further includes the step of implanting the mesh in a mammal so that some portions of the filament align approximately to the load axis that the mesh will be subject to. Following the contacting step, the method further includes the step of cutting the mesh parallel to the mandrel's central axis to remove the mesh from the mandrel as a flat fabric patch. Following the cutting step, the method further includes the step of sterilizing the flat fabric patch. Following the sterilizing step, the method further includes the step of implanting the flat fabric patch in a mammal so that some portions of the filament align approximately to the load axis that the mesh will be subject to.

A further aspect of the invention relates to an implantable fabric having biocompatible filaments consisting of a bio-absorbable material arranged in a weave pattern, wherein the filaments are bonded at intersecting points, and wherein the weave pattern includes pores formed in between the filaments to form a biocompatible macroporous mesh.

The weave pattern comprises one set of biocompatible filaments wound in a first helical direction on a tube and another set of biocompatible filaments wound in a second helical direction on the tube, wherein the one set of filaments intersects the other set of filaments at points which define one dimension of the pores. The tube includes removable pins. The tube and the mesh are disposed on a rotatable and linearly translatable mandrel. Alternatively, the tube and the mesh are disposed in a solvent bath. The solvent is an acid. The bioabsorbable thread is made from collagen, particularly electrochemically compacted collagen.

BRIEF DESCRIPTION OF THE DRAWINGS

The advantages, nature, and various additional features of the invention will appear more fully upon consideration of the illustrative embodiments now to be described in detail in connection with accompanying drawings. In the drawings wherein like reference numerals denote similar components throughout the views.

DETAILED DESCRIPTION OF THE PREFERRED EMBODIMENTS

Figure 1:
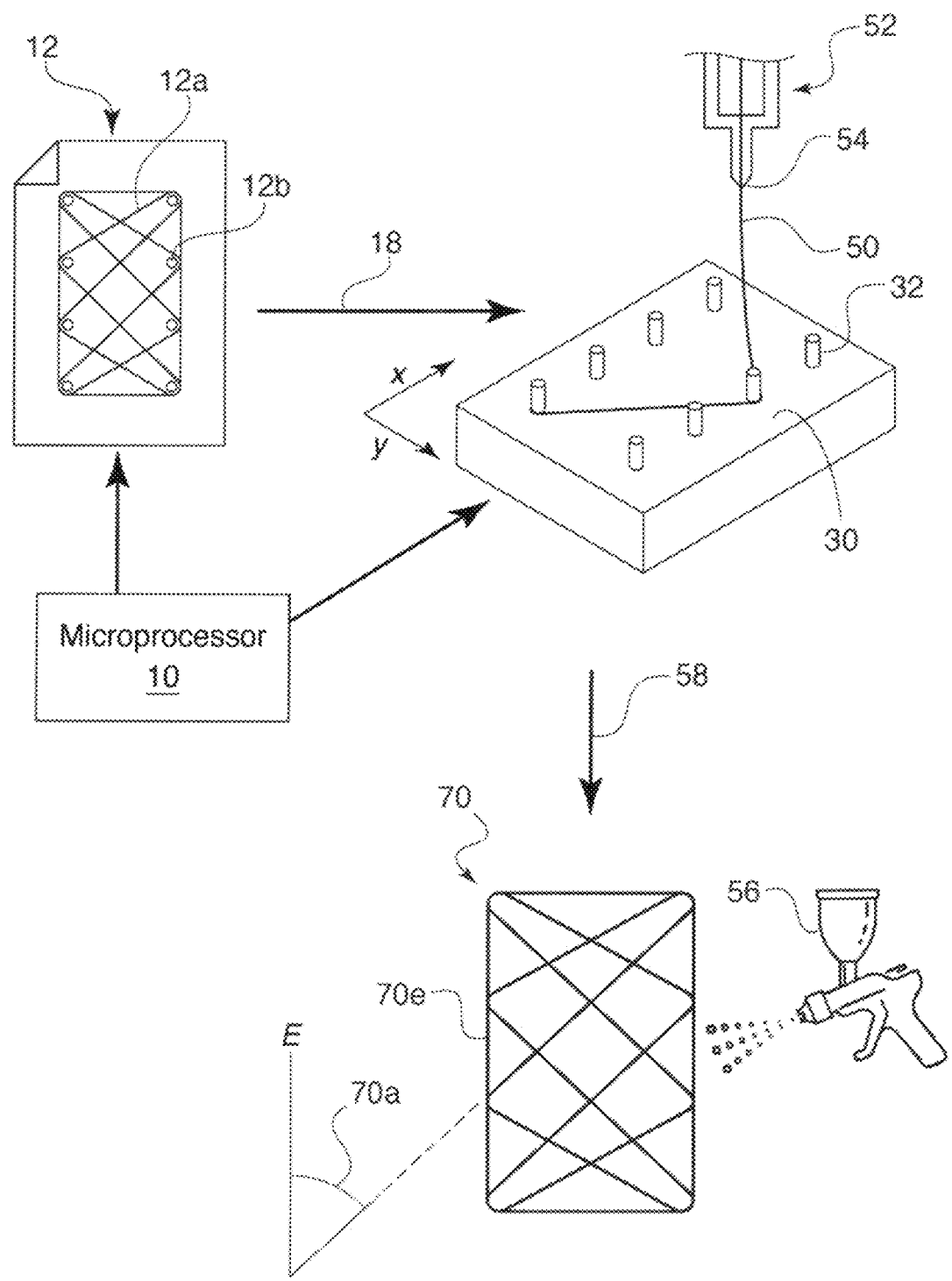
FIG. 1 is a schematic diagram illustrating the system and workflow according to an embodiment of the invention to manufacture a macroporous mesh.

As described above, previous preparations of implantable textiles attempt to balance the mechanical and chemical properties of threads with their level of biocompatibility. The present invention provides a high level of biocompatibility, and in particular seeks to provide an implantable mesh made primarily of a bio-absorbable filament. The bio-absorbable filament is made from naturally occurring materials and therefore does not require and modification of its chemical properties. However, the bio-absorbable material has significantly less tensile strength than the PET and PTFE of the prior art. Accordingly, novel systems and methods are proposed which efficient dispense the bio-absorbable filament and provide variable mesh configurations that possess controllable pore size in combination with angular offset of the filament based on surgical application.

The configuration of the implantable mesh is designed in advance to achieve the stated goals. Based on the intended surgical application, an overall size and shape can be determined. By properly and conservatively dimensioning the implantable mesh the filament material can be conserved. Other factors include pore size, the number or layers of filaments and angularly offsetting filaments to align approximately to the load axis that the mesh will be subject to following implantation. The advance design is embodied in a template or mesh layout. The template can then be mapped to a flat or tubular support surface. In the case of a tubular support, the template is generated by software that accounts for mandrel diameter, desired width, and pore size. The template specifies the location of pins on the mandrel so the design can be wound. In one embodiment, the software executes a reiterative process of adjusting pore size and filament angular offset alternately until the layout is optimized.

Logic device may include, for example, a microprocessor, a single-core processor, a multi-core processor, a microcontroller, a programmable logic device configured to perform processing operations, a digital signal processing (DSP) device, one or more memories for storing executable instructions (e.g., software, firmware, or other instructions), and/or any other appropriate combinations of devices and/or memory to perform any of the various operations described herein. Logic device is configured to interface and communicate with the various components of imaging device to perform various method and processing steps described herein. In various embodiments, processing instructions may be integrated in software and/or hardware as part of logic device, or code (e.g., software and/or configuration data) which may be stored in memory and/or a machine readable medium. In various embodiments, the instructions stored in memory and/or machine readable medium permit logic device to perform the various operations discussed herein and/or control various components of device for such operations.

Memory may include one or more memory devices (e.g., one or more memories) to store data and information. The one or more memory devices may include various types of memory including volatile and non-volatile memory devices, such as RAM (Random Access Memory), ROM (Read-Only Memory), EEPROM (Electrically-Erasable Read-Only Memory), flash memory, fixed memory, removable memory, and/or other types of memory.

Machine readable medium (e.g., a memory, a hard drive, a compact disk, a digital video disk, or a flash memory) may be a non-transitory machine readable medium storing instructions for execution by logic device. In various embodiments, machine readable medium may be included as part of imaging device and/or separate from imaging device, with stored instructions provided to imaging device by coupling the machine readable medium to imaging device and/or by imaging device downloading (e.g., via a wired or wireless link) the instructions from the machine readable medium (e.g., containing the non-transitory information).

As can be seen in FIG. 1, the microprocessor 10 determines a mesh layout 12 that includes a filament path 12a based on filament retention point 12b. The retention points are mapped 18 to a support surface 30 so that pins 32 can be set in a configuration that corresponds to the retention points 12b.

In one embodiment, the pins are integrally formed with the support surface. This type of support surface can be custom fabricated in a variety of ways. For example, the support surface with integral pins can be molded from a medical grade polymer material. A medical grade metal block can be machined to remove material. The pins can be 3D printed from a medical grade material. The microprocessor 10 can convert the filament retention points with computer-aided design or computer-aided manufacturing (CAD/CAM) software to a three-dimensional model which can be interpreted by a computer numerical control (CNC) machine to mill the support surface or mill a die to mold the support surface.

The biocompatible thread or filament 50 is provided from a dispenser 52 with a precision tip 54. The support surface 30 and tip 54 are translated with respect to each other to wind the filament 50 around pins 32 to form a mesh based on layout 12. The translational motion between surface 30 and tip 54 may be two-dimensional or three-dimensional. For example, dispenser 52 may be mounted on a 3D articulating robotic arm. The microprocessor 10 can produce a set of instructions to move the robotic arm and dispense filament along filament path 12a around pins 32.

In certain instances, it may be desirable to have dispenser 52 mounted stationary to simplify monitoring and resupplying of the filament. Support surface 30 may be mounted on a cross slide, or X-Y table for movement. FIG. 1 shows exemplary motion of support surface 30 as moving side-to-side in the X direction, and moving up-and-down in the Y direction. The microprocessor 10 can produce a set of instructions to move the X-Y table so that dispensed filament is wound around pins 32 following filament path 12*a*. Additional filament could be wound along part of, or all, of the path, or along the perimeter. Once completed the mesh is contacted with a solution 56 to dissolve the outer surface so that intersecting filaments bond to each other. The solution comprises an acidic solution having a pH in the range of 2.5 to 3.5. Such acidic solutions may be selected from: 0.5 mg/mL of L-Ascorbic acid in deionized H$_2$O adjusted to a pH of 3.3; or an acidic collagen solution comprising 5 mg/mL collagen solubilized in hydrochloric acid (HCl) solution in deionized H$_2$O adjusted to a pH of 2.7; or HCl in deionized H$_2$O adjusted to a pH of 2.7. Alternatively, the wound filament can be contacted with a UV crosslinkable biocompatible hydrogel to achieve bonding.

The bonded filaments are then removed from the support 58 to provide a macroporous mesh 70. In the depiction, additional filament is shown around the perimeter. An edge 70*e*, E of the mesh provides a reference line from which an angular offset 70*a*, AO is measured. The macroporous mesh 70 is sterilized and then is ready for implantation. The angularly offset portions of the filament are implanted to align approximately to the load axis that the mesh will be subject to.

Figure 2A:
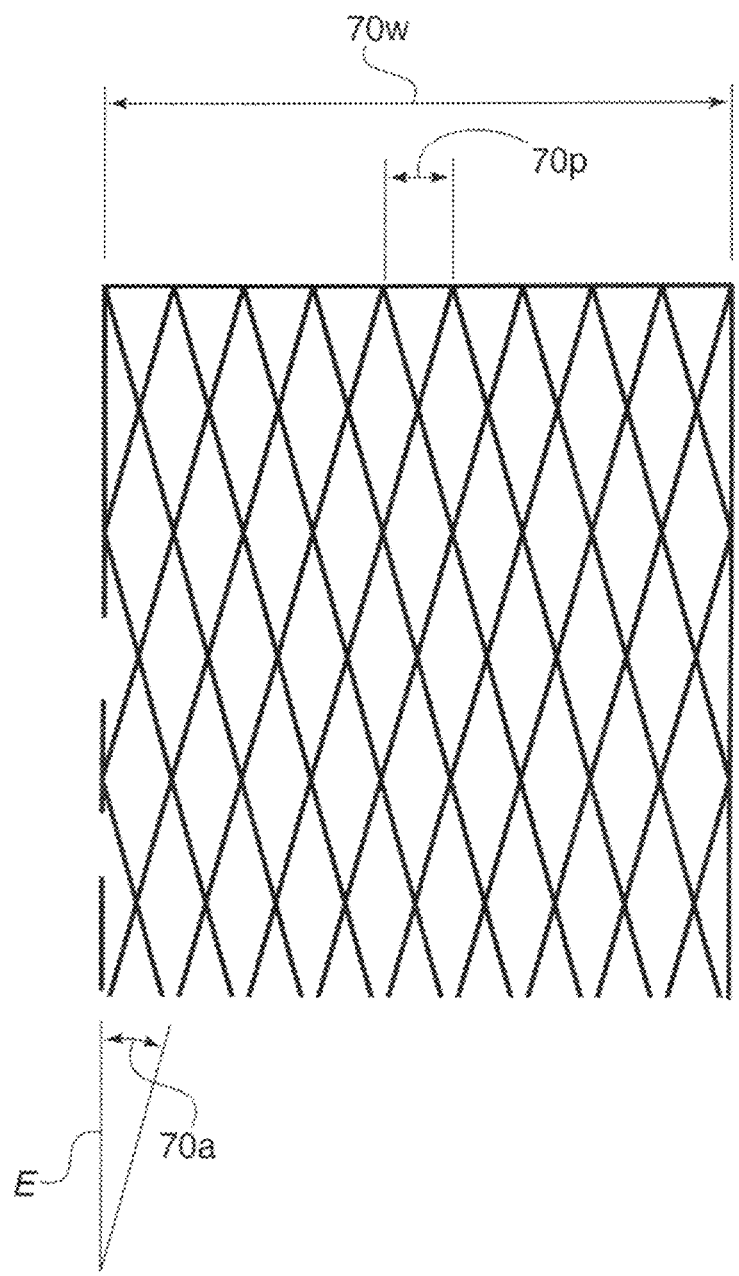
FIG. 2A is a diagram of one embodiment of a mesh layout.
Figure 2B:
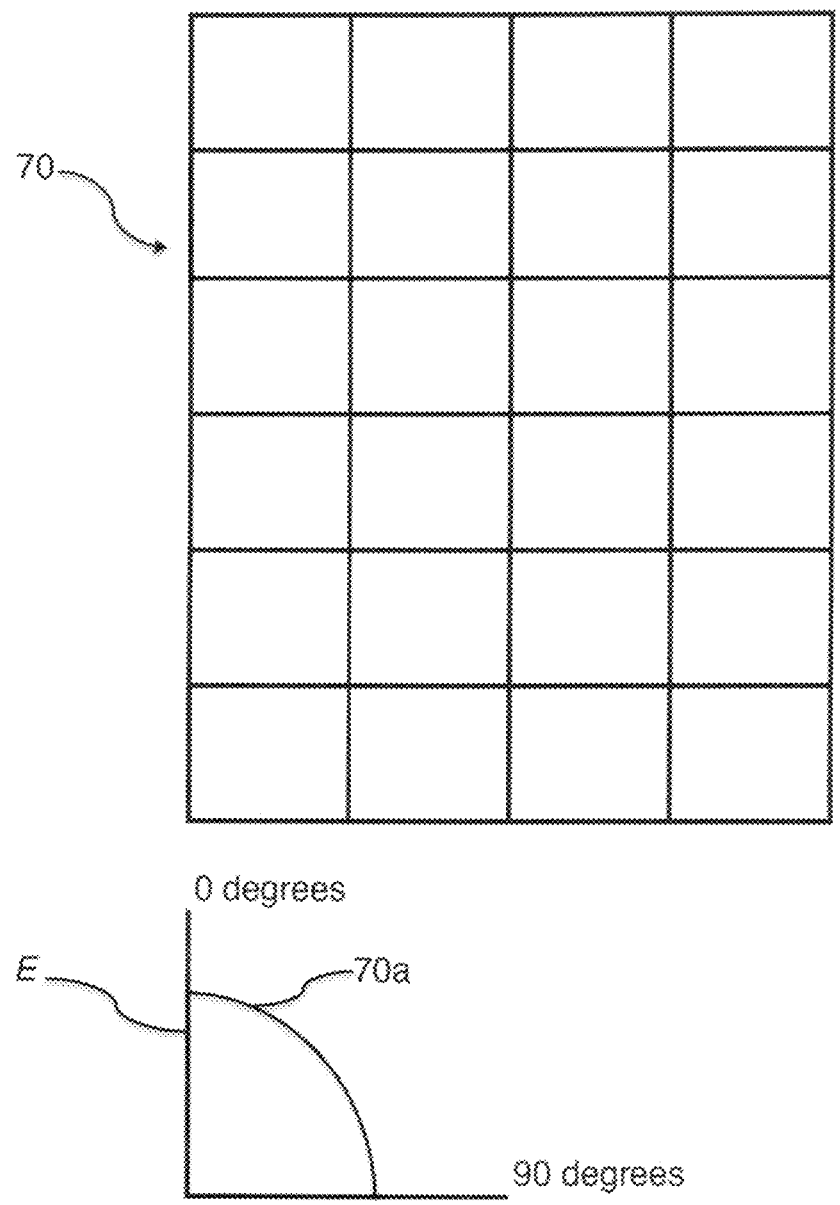
FIG. 2B is a diagram of an alternate mesh layout.

FIG. 2A shows a section of a mesh layout design template for a filament wound fabric. The overall width 70*w* is 1.2 cm, with a 1.3 mm pore size (width 70*p* of each diamond). A portion of the filaments extend at an angular offset 70*a* with respect to and edge E of the fabric patch. Other portions of filament will extend at a complementary angular offset from the opposed edge. This will create diamonds of filament that border the pores. The template is generated by software that accounts for mandrel diameter, desired width, and pore size. The template is used to place pins on the mandrel so the design can be wound. FIG. 2B shows an alternate mesh 70 layout design template for a filament wound fabric, where the filaments extend from pin-to-pin in horizontal and vertical directions. In this embodiment, some portion of the filaments extend at 0 degrees and 90 degrees with respect to an edge (E) of the fabric, while in FIG. 2A some portion of the filaments extended at an acute angle. The filament can extend in any direction between two flexibly locatable pins. In geometric terms, the angular offset 70*a* of the filaments can vary between 0 degrees and +90 degrees with respect to the right edge (E), and between 0 degrees and −90 degrees with respect to the left edge.

Figure 3:
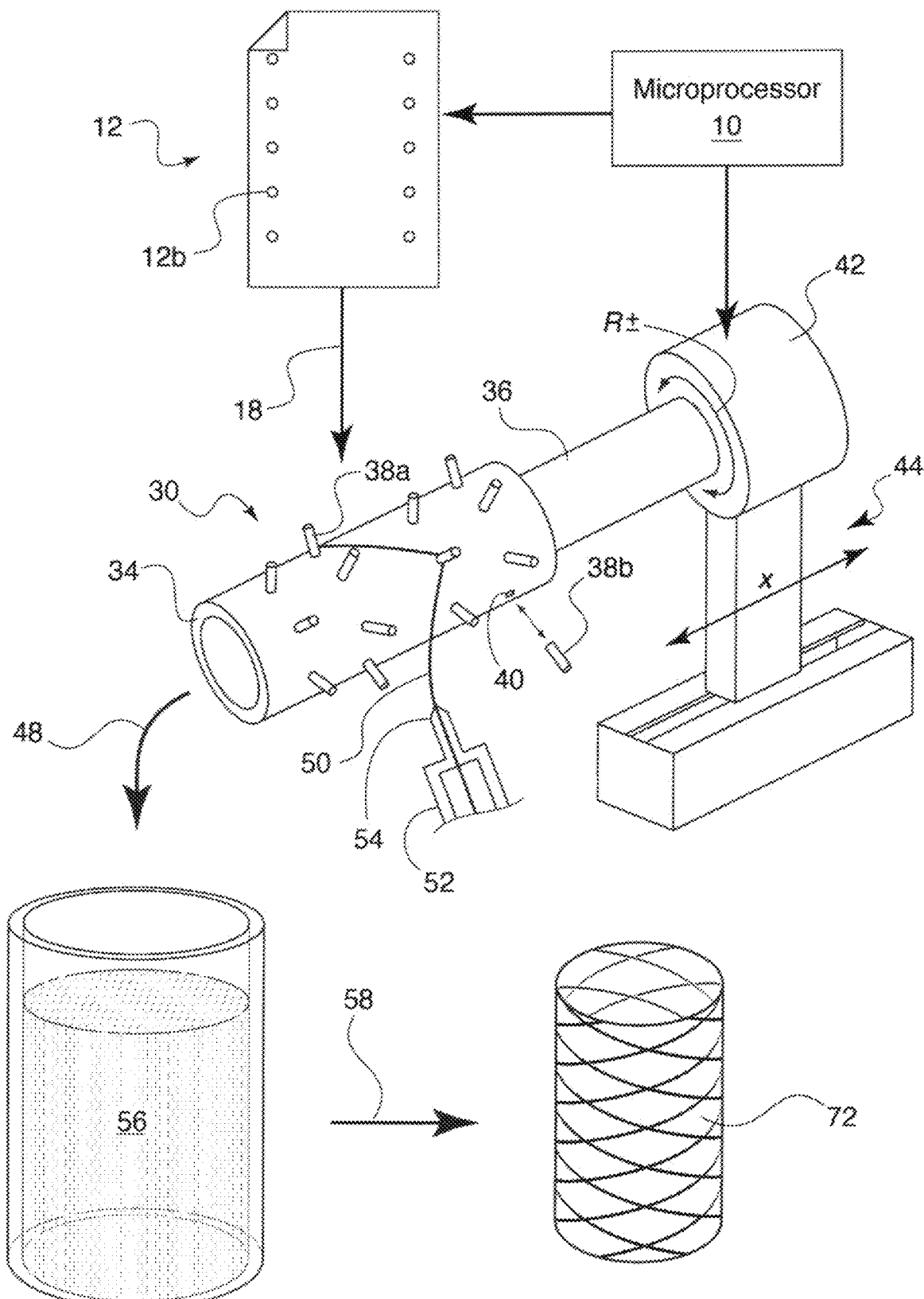
FIG. 3 is a schematic diagram illustrating an alternate embodiment of the system and workflow to manufacture a macroporous mesh.

FIG. 3 shows a preferred embodiment of the support surface 30, which is fashioned as a tube 34 mounted on a mandrel 36. Mandrel 36 is operatively coupled to a rotary drive 42, for example, a servo motor capable of rotational movements both clockwise and counter-clockwise accurate to 1 degree (out of 360 degrees). The servo motor is mounted on a sled of a linear drive 44 capable of linear movement back and forth in increments equivalent to that of the servo motor.

The microprocessor 10 determines a mesh layout 12 that includes filament retention point 12*b*. The retention points are mapped to the cylindrical tube surface so that pins 38 can be set in a configuration that corresponds to the retention points 12*b*. Tube 34 is depicted with one set of pins 38*a* mounted. Tube 34 may be provided with apertures 40 to allow a set of pins 38*b* to be removably mounted. In filament winding we take a length of collagen thread and wind it on a cylindrical tube.

Filament 50 is fed from a dispenser 52 that is stationary. Computer controlled motors turn and translate the mandrel, winding the thread on the mandrel in a pre-specified pattern. Pins placed on the mandrel hold the thread in place wherever the pattern changes the thread direction The microprocessor 10 can produce a set of instructions to rotate the mandrel and axially displace the servo motor so that dispensed filament is wound around pins 32*a* following the filament path. Additional filament could be wound along part of, or all, of the path, or along the perimeter. During one winding phase the mandrel is rotated in a first direction and translated in a first axial direction to wind filament along a first helical path. During another winding phase the mandrel is rotated in a opposite direction and translated in an opposite axial direction to wind filament along a second helical path that intersects with the first helical path to form diamond shapes that border the pores.

Once the full pattern is completed, the mandrel is dipped in a mild acid and allowed to dry. The acid slightly dissolves the collagen threads, allowing them to melt into each other wherever there is an overlap point. The pattern is then cut off the mandrel and flattened into a strip. Because of the bonds formed at each vertex the full pattern coheres and is strong. The mandrel can be any arbitrary diameter, which sets the length of the fabric. The placement of the pins defines the pattern width and the thread angles, which in turn define the pore size. In addition to the primarily longitudinal direction of the threads, we also use horizontal thread sections that act to keep the ends of the pattern from fraying and mark where to cut. To increase the strength and/or thickness, multiple passes can be wound to layer two or more sets of threads. These will also be bonded by the acid. The thread must be uncrosslinked during filament winding in order for the threads to melt and bond when exposed to the acidic solution. Once the mesh is bonded, dried and removed from the support surface it may be crosslinked.

To achieve contact, tube 34 may be removed from mandrel 36 and submerged 48 in a solution bath. The pins are then removed from the tube so that the bonded mesh can be slid off the tube 58 in one piece as a macroporous sleeve 72. The sleeve can be cut open to form a rectangular mesh. The bonded mesh is sterilized prior to implantation. Various methods of sterilization may be utilized including temperature sterilization, chemical sterilization, electromagnetic radiation sterilization or particle bean sterilization. Methods for temperature sterilization include high temperature autoclaving or low temperature liquid nitrogen. Solutions for chemical sterilization include ethylene oxide or peracetic acid. Wavelengths for electromagnetic sterilization include gamma rays. Particles for beam sterilization include electron beams.

Figure 4:
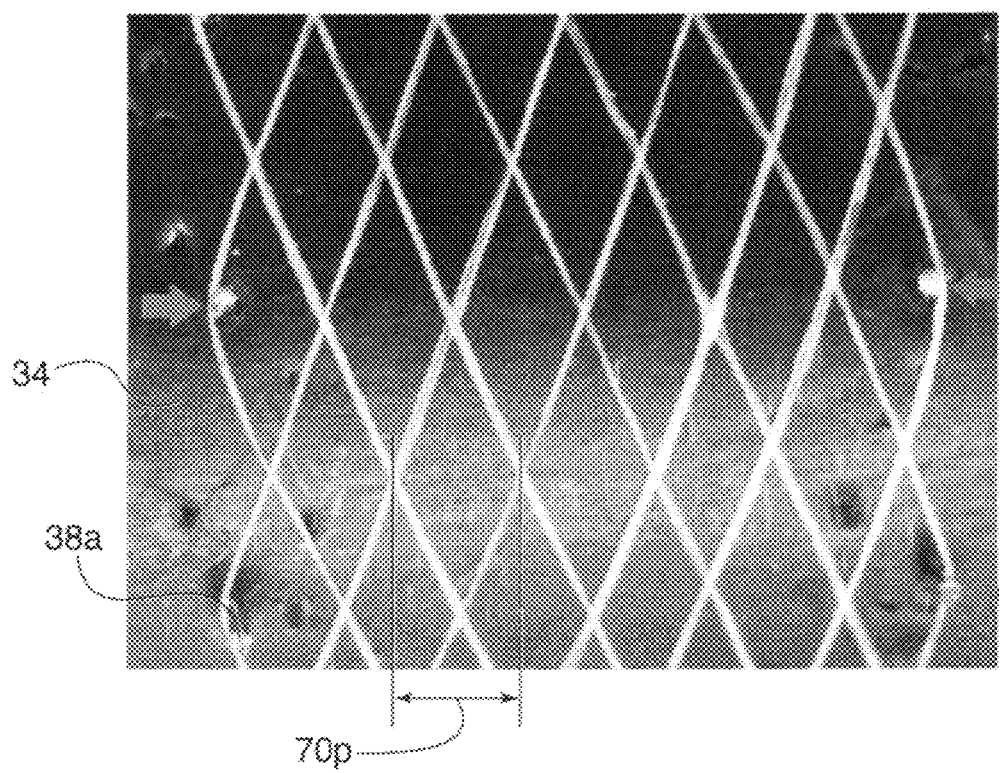
FIG. 4 is a micrograph of a macroporous mesh wound around the pins on the tube.

FIG. 4 is a micrograph showing details of filament wound collagen thread around pins 38*a* on a tube 34. Pore size (width of each diamond 70*p*) is 2.17 mm.

Figure 5:
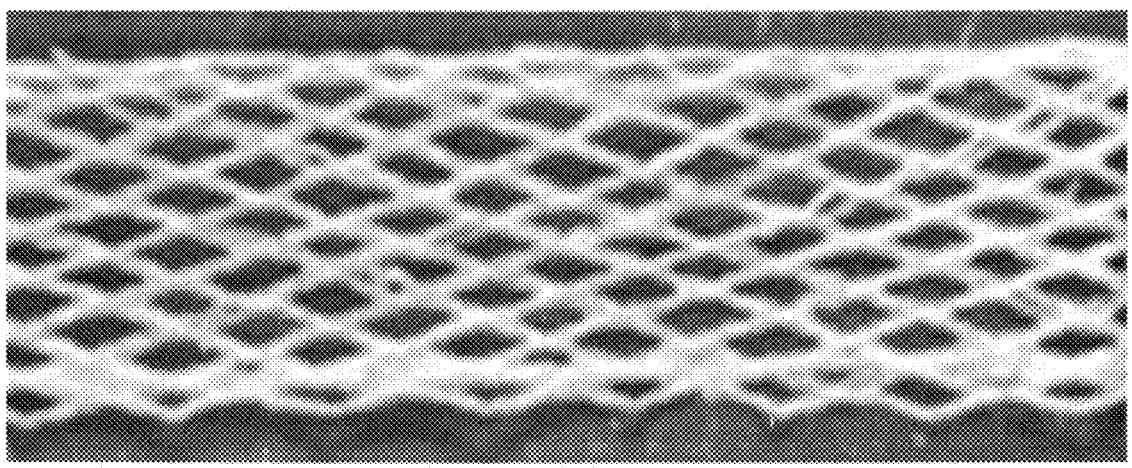
FIG. 5 is a micrograph of a macroporous sleeve

FIG. 5 is a micrograph showing a section of a 13 mm wide fabric patch after filament winding, bonding and removal from the mandrel. This design is double-layered and includes additional longitudinal threads on the left and right sides for extra strength. The filament wound macroporous mesh sleeve can then be cross-linked, packaged, and sterilized to create a finished medical device.

Figure 6:
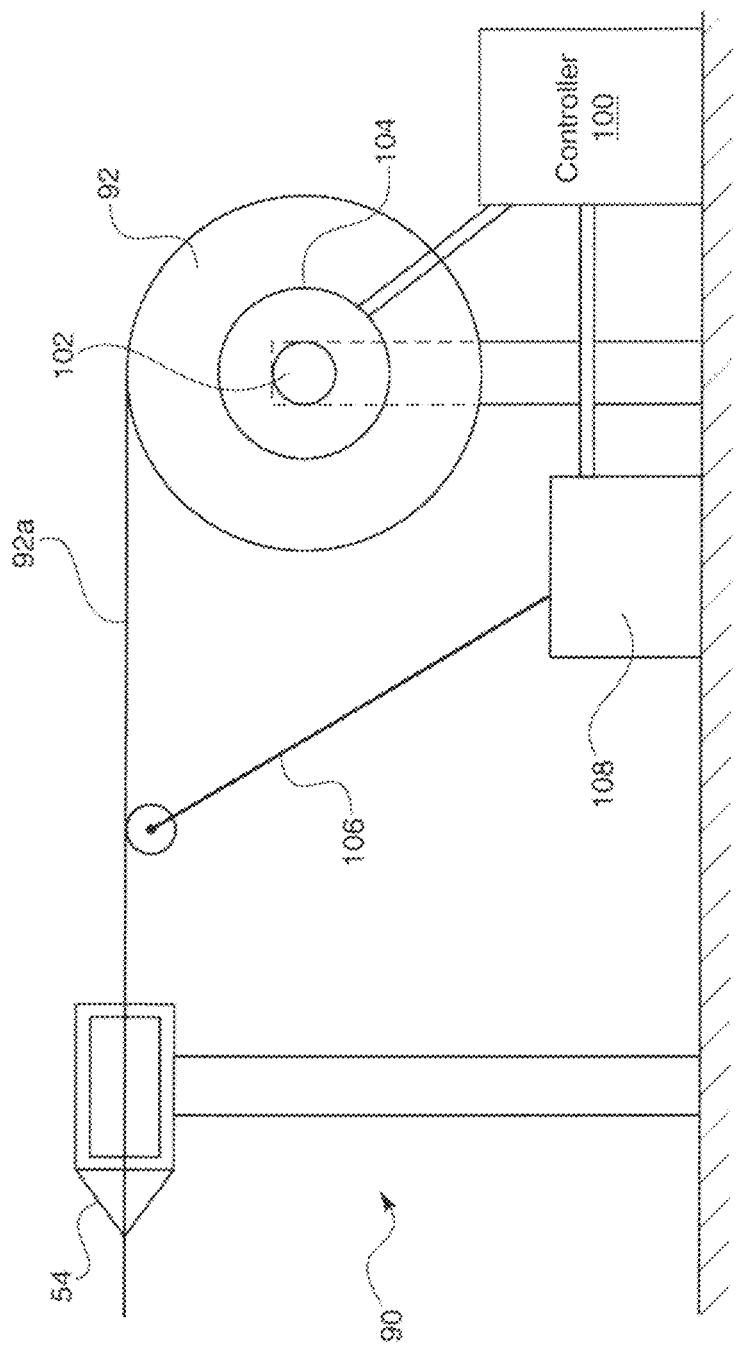
FIG. 6 is a schematic diagram of a filament dispenser with tensioner.

An embodiment of the dispenser 90 is shown in FIG. 6. A spool 92 of thread feeds filament 92*a* to the tip 54 as shown in FIGS. 1 and 3. The spool 92 is mounted on an axle 102. Spool 92 is coupled to axle 102 via an electronic brake 104 or clutch, which can vary the friction applied to the spool. A dancer arm 106 measures the actual tension on filament 92*a* which is detected in arm sensor 108. A dispenser controller 100 uses the detected tension from sensor 108 to adjust the friction level of electronic brake 104 to maintain the tension on filament 92*a* at the desired level. The filament has a tensile strength in the range of 1 N to 4 N, and more particularly in the range of 2.5 N to 3.5 N. Accordingly, the filament is dispensed at a tension within the range of 0.1 N to 1 N, and more particularly in the range of 0.5 N to 0.6 N. Yarns containing two or more strands of filament may be dispensed at higher tensions. Of particular usefulness in practicing the invention is filament prepared according to U.S. Pat. No. 10,017,868 entitled Electrochemical Processing of Materials, Methods and Production, the contents of which is incorporate herein by reference thereto. These collagen filaments are prepared by placing a solution of collagen molecules with ampholytic nature in a groove bordered on either side with an electrode. A current is applied to the electrodes which passes through the solution to form electrochemically aligned strands or filaments.

Figure 7:
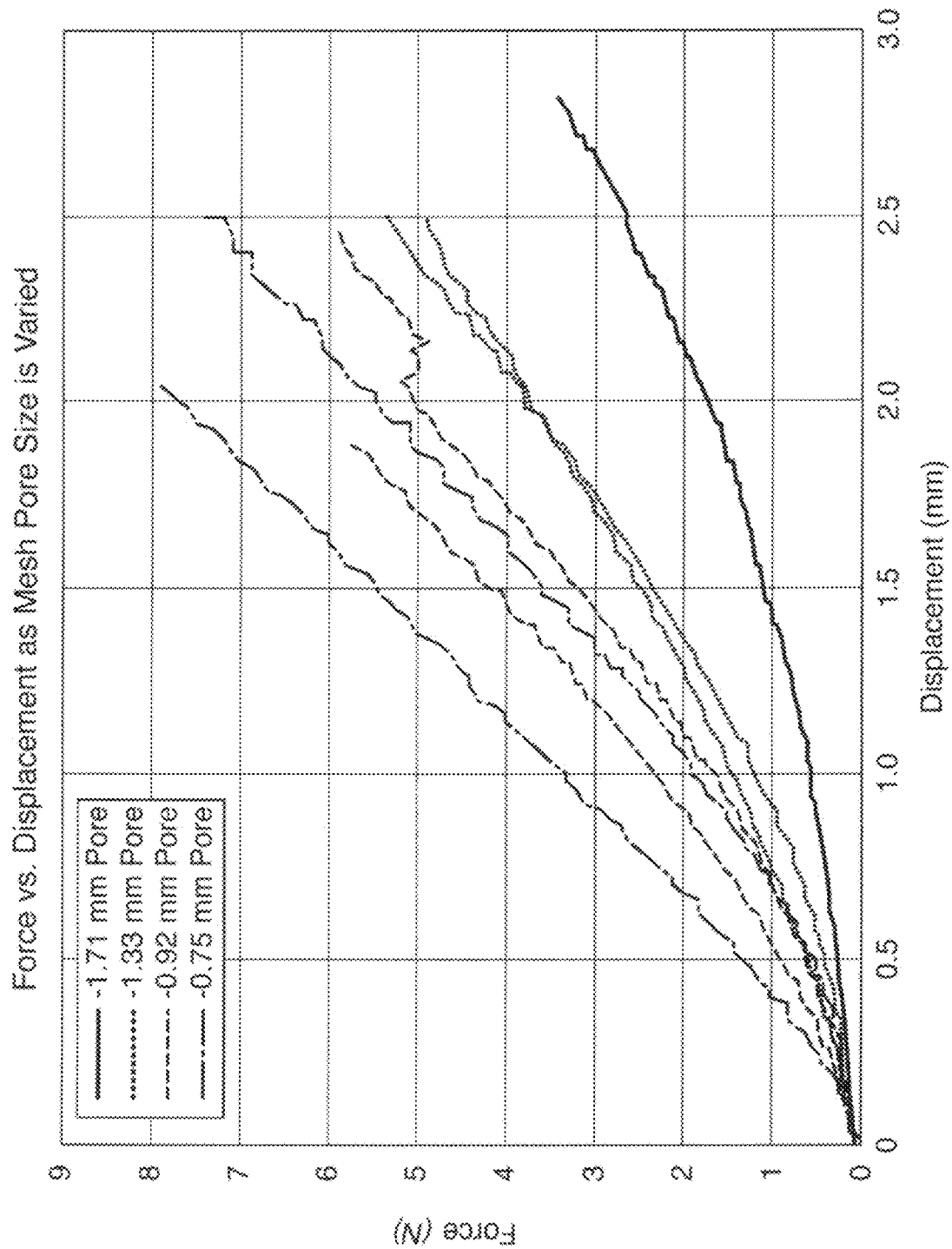
FIG. 7 is a graph illustrating the relationship between force and displacement as pore size is varied.

The properties of the fabric or macroporous mesh can be modulated by the choice of pore size, as shown in FIG. 7, which shows how porosity affects the mechanical properties. Porosity may also affect tissue ingrowth in vivo, which is being currently explored in a rat subcutaneous implant study. The graph shows Force vs. displacement to failure curves for hydrated, cross-linked fabric patches of varying porosities manufactured according to the invention. In general, the smaller the pore size the stronger the material.

Having described preferred embodiments for (which are intended to be illustrative and not limiting), it is noted that persons can make modifications and variations skilled in the art in light of the above teachings. The apparatus may include mandrels and correspondingly fitted tubes of various sizes differing independently in circumference and length. In practicing the method, alternate or additional steps may be included that do not alter the purpose of the invention. The use of equivalent systems, equipment and steps other than those specified is intended to be included within the scope of the invention. It is therefore to be understood that changes may be made in the particular embodiments of the invention disclosed which are within the scope and spirit of the invention as outlined by the appended claims. Having thus described the invention with the details and particularity required by the patent laws, the features intended to be protected by this application are as follows.

What is claimed is:

1. A method of manufacturing an implantable mesh comprising the steps of:
   determining a mesh layout having filament retention points;
   providing a support surface with pins in a configuration that corresponds to the filament retention points;
   feeding a biocompatible filament by a tensioner to a dispenser tip; and
   translating the support surface with respect to the dispenser tip, wherein the support surface is translated in two dimensions independent from each other to wind the biocompatible filament around the pins to form an implantable macroporous mesh having a pore size based on the determined mesh layout.

2. The method of claim 1, wherein said translating step includes winding the biocompatible filament around the pins in a preselected order to arrange some portions of the filament at an angular offset with respect to an edge of the implantable mesh, wherein the angularly offset portions of the filament are adapted to align approximately to a load axis that the macroporous mesh will be subject to following implantation.

3. The method of claim 2, wherein the support surface is machined to provide fixed pins in the configuration, and wherein filament is would around the pins to form a perimeter for the mesh layout.

4. The method of claim 1, wherein the filament comprises a bio-absorbable material.

5. The method of claim 4, wherein the filament consists of collagen.

6. The method of claim 4, wherein the filament comprises electrochemically aligned collagen.

7. The method of claim 4, wherein following said translating step the method further comprises the step of:
   contacting the formed mesh with a biocompatible solution to dissolve the biocompatible filament so that intersecting filament sections bond to each other.

8. The method of claim 7, wherein following said contacting step, the method further includes the step of:
   cutting the mesh parallel to the mandrel's central axis to remove the mesh from the mandrel as a flat fabric patch.

9. The method of claim 7, wherein following said contacting step, the method further includes the step of:
   sterilizing the flat fabric patch, and packaging the sterilized patch so that it is adapted for implanting in a mammal so that some portions of the filament align approximately to the load axis that the mesh will be subject to.

10. The method of claim 4, wherein the support surface comprises a cylindrical tube mounted on a mandrel having a central axis, and wherein translating the support surface comprises displacing the mandrel along the central axis and independently rotating the mandrel around the central axis.

11. The method of claim 10, wherein the step of providing a support surface further comprises fabricating the tube with apertures so that pins can be removably placed in various configurations.

12. The method of claim 11, wherein following said translating step the method further comprises the step of:
   dipping the mandrel into a solution to dissolve the biocompatible filament so that intersecting filament sections bond to each other.

13. The method of claim 12, wherein following said contacting step, the method further includes the step of:
   removing the pins and sliding the mesh off the mandrel as a sleeve.

14. The method of claim 13, wherein following said removing step, the method further includes the step of:
   sterilizing the mesh.

15. The method of claim 14, wherein following said sterilizing step, the method further includes the step of:
   packaging the sterilized mesh so that it is adapted for implanting in a mammal so that some portions of the filament align approximately to the load axis that the mesh will be subject to.

16. The method of claim 1, wherein said feeding step comprises feeding a biocompatible filament consisting of bioabsorbable compacted aligned collagen by a tensioner to a dispenser tip at a tension within the range of 0.1 N to 1 N.

17. The method of claim 1, wherein following said translating step the method further comprises the step of:
   contacting the formed mesh with an acidic solution having a pH in the range of 2.5 to 3.5 to dissolve the biocompatible filament so that intersecting filament sections bond to each other.

* * * * *